US008932858B2

(12) United States Patent
Baker et al.

(10) Patent No.: US 8,932,858 B2
(45) Date of Patent: *Jan. 13, 2015

(54) MODIFIED POLYSACCHARIDE FOR CELL CULTURE AND RELEASE

(75) Inventors: Wendy A. Baker, Bath, NY (US); Dana C. Bookbinder, Corning, NY (US); Theresa Chang, Painted Post, NY (US); Robert R. Hancock, Jr., Corning, NY (US)

(73) Assignee: Corning Incorporated, Corning, NY (US)

( * ) Notice: Subject to any disclaimer, the term of this patent is extended or adjusted under 35 U.S.C. 154(b) by 1089 days.

This patent is subject to a terminal disclaimer.

(21) Appl. No.: 12/397,809

(22) Filed: Mar. 4, 2009

(65) Prior Publication Data

US 2009/0227024 A1    Sep. 10, 2009

Related U.S. Application Data

(60) Provisional application No. 61/068,576, filed on Mar. 7, 2008.

(51) Int. Cl.
*C12N 5/02* (2006.01)
*C08B 11/20* (2006.01)
*C12N 5/00* (2006.01)

(52) U.S. Cl.
CPC .............. *C08B 11/20* (2013.01); *C12N 5/0068* (2013.01); *C12N 2533/78* (2013.01)
USPC ........ 435/378; 435/178; 435/325; 435/305.1; 435/308.1; 435/307.1

(58) Field of Classification Search
USPC ........ 435/378, 178, 325, 305.1, 308.1, 307.1; 3/178, 325, 305.1, 308.1, 307.1
See application file for complete search history.

(56) References Cited

U.S. PATENT DOCUMENTS

| | | | |
|---|---|---|---|
| 4,391,912 A | 7/1983 | Yoshida et al. | 435/241 |
| 5,079,168 A | 1/1992 | Amiot | 437/284 |
| 5,281,660 A | 1/1994 | Bryhan et al. | 525/50 |
| 5,693,537 A | 12/1997 | Wilson et al. | 435/401 |
| 5,712,154 A | 1/1998 | Mullon et al. | 435/297.4 |
| 5,731,417 A | 3/1998 | Swiderek et al. | 530/356 |
| 5,804,431 A | 9/1998 | Palsson | 435/235.1 |
| 5,874,301 A | 2/1999 | Keller et al. | 435/325 |
| 5,981,211 A | 11/1999 | Hu et al. | 435/41 |
| 6,258,586 B1 * | 7/2001 | Jussila et al. | 435/252 |
| 6,479,283 B1 | 11/2002 | Månsson et al. | 435/325 |
| 6,821,772 B2 | 11/2004 | Barbera-Guillem et al. | 435/297.5 |
| 7,041,505 B2 | 5/2006 | Tsuzuki et al. | 435/401 |
| 7,092,154 B2 | 8/2006 | Yasuda et al. | 359/398 |
| 7,189,526 B2 | 3/2007 | Kojima et al. | 435/30 |
| 7,229,820 B2 | 6/2007 | Wilson | 435/284.1 |
| 7,256,042 B2 | 8/2007 | Rambhatla et al. | 435/377 |
| 7,282,366 B2 | 10/2007 | Rambhatla et al. | 435/377 |
| 2002/0143160 A1 * | 10/2002 | Sunamoto et al. | 536/20 |
| 2004/0248291 A1 | 12/2004 | Yamamoto et al. | 435/325 |
| 2005/0019380 A1 | 1/2005 | Hoon et al. | 424/445 |
| 2005/0058687 A1 | 3/2005 | Guarino et al. | 424/426 |
| 2005/0090005 A1 | 4/2005 | Kojima et al. | 435/404 |
| 2005/0130302 A1 | 6/2005 | Nakauchi et al. | 435/372 |
| 2005/0164377 A1 | 7/2005 | Miyabayashi et al. | 435/366 |
| 2005/0196828 A1 | 9/2005 | Zheng et al. | 435/51 |
| 2005/0244365 A1 | 11/2005 | Labib et al. | 424/78.18 |
| 2005/0255327 A1 | 11/2005 | Chaney et al. | 428/448 |
| 2005/0265980 A1 | 12/2005 | Chen et al. | 424/93.7 |
| 2005/0287670 A1 | 12/2005 | Gulliver et al. | 435/455 |
| 2006/0003442 A1 | 1/2006 | Gong et al. | 435/325 |
| 2006/0024823 A1 | 2/2006 | Ishikawa et al. | 435/325 |
| 2006/0160066 A1 | 7/2006 | Bhatia et al. | 435/4 |
| 2006/0194313 A1 * | 8/2006 | Pierce et al. | 435/325 |
| 2006/0281172 A1 | 12/2006 | Kuwabara et al. | 435/305.2 |
| 2007/0031966 A1 | 2/2007 | Dressler et al. | 435/369 |
| 2007/0054043 A1 | 3/2007 | Gaserod et al. | 427/244 |
| 2007/0059763 A1 | 3/2007 | Okano et al. | 435/7.1 |
| 2007/0148767 A1 | 6/2007 | Yang et al. | 435/325 |
| 2008/0280807 A1 * | 11/2008 | Grainger et al. | 510/522 |

FOREIGN PATENT DOCUMENTS

| | | | | |
|---|---|---|---|---|
| EP | 0566911 A | 10/1993 | | C09D 7/00 |
| EP | 1 035 134 | 9/2000 | | |
| WO | WO9856825 A | 12/1998 | | C08B 11/193 |

OTHER PUBLICATIONS

Gu, Q-M. ACS Symposium Series (2003) 840(Biocatalysis in Polymer Science): 243-252.*

E. Akiyama, et al., "Thickening properties and emulsification mechanisms of new derivatives of polysaccharides in aqueous solution", *Journal of Colloid and Interface Science*, 2005, vol. 282, pp. 448-457.

I. Erol, "Copolymerization of Two New Kinds of Methacrylate Monomers and Determination of Monomer Reactivity Ratios", *Journal of Applied Polymer Science*, 2006, vol. 100, pp. 1864-1874.

Ihara, et al., "Solution Properties of a Novel Polysaccharide Derivative", *Chem. Lett.*, 2004, vol. 33, No. 9, p. 1094.

K. Kawakami, et al., "Salt Tolerance of an Aqueous Solution of a Novel Amphiphilic Polysaccharide Derivative", *Langmuir*, 2006, vol. 22, pp. 3337-3343.

E.L. LeCluyse, "Human hepatocyte culture systems for the in vitro evaluation of cytochrome P450 expression and regulation", *European Journal of Pharmaceutical Sciences*, 2001, vol. 13, pp. 343-368.

A. Maestro, et al., "Shear thinning and thixotropy of HMHEC and HEC water solutions", *J. Rheol.*, 2002, vol. 46, No. 6, pp. 1445-1457.

(Continued)

*Primary Examiner* — Susan Hanley
(74) *Attorney, Agent, or Firm* — John L. Haack (57) ABSTRACT

Hydrophobically modified polysaccharide compositions, articles incorporating the compositions, and methods for cell culture, automatic release of cells, and release of cell culture coating from a substrate or the cell culture articles incorporating the coating compositions, as defined herein.

20 Claims, 5 Drawing Sheets

(56) References Cited

OTHER PUBLICATIONS

P.V. Moghe, et al., "Culture matrix configuration and composition in the maintenance of hepatocyte polarity and function", *Biomaterials,* 1996, vol. 17, pp. 373-385.

C. Vinatier, et al., "A silanized hydroxypropyl methylcellulose hydrogel for the three-dimensional culture of chondrocytes", *Biomaterials,* 2005, vol. 26, pp. 6643-6651.

L.M. Zhang, "Cellulosic associative thickeners", *Carbohydrate Polymers,* 2001, vol. 45, pp. 1-10.

* cited by examiner

MODIFIED POLYSACCHARIDE FOR CELL CULTURE AND RELEASE

CLAIMING BENEFIT OF PRIOR FILED U.S. APPLICATION

This application claims the benefit of U.S. Provisional Application Ser. No. 61/068,576, filed on Mar. 7, 2008. The content of this document and the entire disclosure of any publication, patent, or patent document mentioned herein is incorporated by reference.

BACKGROUND

The disclosure is related to methods and articles for cell culture and cell release.

SUMMARY

The disclosure provides hydrophobically modified polysaccharide compositions, articles incorporating the compositions such as coated substrates, and methods for cell culture and automatic cell release from the cell culture articles incorporating the compositions. The disclosure provides a composition, an article, and a method having excellent cell culture properties for either anchorage-dependent cells or anchorage-independent cells, for example, non-propagating cells, such as primary hepatocyctes, where desirable aspects of cell function are retained, such as albumin production, and having excellent cell-cell adhesion and excellent cell-substrate adhesion properties. The coated substrates can be, for example, controllably transient, ephemeral, fugitive, or self-releasing.

DETAILED DESCRIPTION

Various embodiments of the disclosure will be described in detail with reference to drawings, if any. Reference to various embodiments does not limit the scope of the invention, which is limited only by the scope of the claims attached hereto. Additionally, examples in this specification are not limiting and merely set forth some of the many possible embodiments for the claimed invention.

Definitions

"Assay," "assaying" or like terms refers to an analysis to determine, for example, the presence, absence, quantity, extent, kinetics, dynamics, or type of a cell's response to an exogenous stimuli, such as a ligand candidate compound, culture media, substrate coating, or like considerations.

"Attach," "attachment," "adhere," "adhered," "adherent," "immobilized", or like terms generally refer to immobilizing or fixing, for example, a surface modifier substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with cells with a surface, such as a biosensor surface or a culture well surface.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell or a cell line or a cell system, such as a prokaryotic or eukaryotic cell, which weakly interacts, or associates or contacts with the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" refers to the culturing of cells derived from multicellular eukaryotes, especially animal cells, but also to the culturing of complex tissues, organs, pathogens, or like systems.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of cells and can include more than one type of cells (or differentiated forms of a single type of cell), which interact with each other, thus performing a biological, physiological, or pathophysiological function. Such cell system can include, for example, an organ, a tissue, a stem cell, a differentiated hepatocyte cell, and like cell systems.

"Tunable," "tuned," or like terms refer to, for example, programmed-release or self-release coating compositions of the disclosure and refers to the capability to preselect or predict coating release and cell release properties.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing embodiments of the disclosure, refers to, for example, variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities.

"Consisting essentially of" in embodiments refers, for example, to a composition, a method of making or using a composition, formulation, or composition on the surface of cell culture article, and like articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand or drug candidate, or like structure, material, or process variable selected. Items that may materially affect the basic properties of the components or steps of the disclosure or that may impart undesirable characteristics to the present disclosure include, for example, decreased affinity of the cell for the coated cell culture surface at the outset, decreased affinity of the substrate surface for the cell culture coating, abnormally decreased or increased affinity of a pathogen for a cultured cell, anomalous or contrary cell activity in response to a ligand candidate or like stimulus, and like characteristics. In some instances, the foregoing examples of undesirable characteristics can instead be highly desirable and beneficial in cell culture applications of the present disclosure, such as discovery of conditions or coatings that decrease the affinity of a cell for a surface coating, or decrease the affinity of the surface coating for a substrate providing for example, enhanced released properties.

The indefinite article "a" or "an" and its corresponding definite article "the" as used herein means at least one, or one or more, unless specified otherwise.

Specific and preferred values disclosed for components, ingredients, additives, cell types, pathogens, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

The disclosure provides a non-animal based cell culture and cell release substrate, such as for mammalian cells, having cell function that more closely resembles in vivo-like behavior. For example, the in vitro culture of hepatocytes can be useful in the drug discovery processes (e.g., predictive ADMETox) (ref. 1) since drugs can be converted to more toxic intermediates and interact with other compounds (e.g., drugs) after metabolism by the CYP450 enzyme in the liver as part of the detoxification process. However, primary hepatocyte cells in vitro can quickly lose function, including albumin production and CYP450 activity, which largely controls the cells ability to metabolize drug molecules. Toxicity and drug interaction studies with these cells are typically less informative.

Cellulose is a linear polymer of β-glucose linked together via β(1→4) glycosidic bonds. Cellulose is commonly found in plant cell walls and is responsible for cell well rigidity. The high tensile strength of cellulose arises from the strong hydrogen bonding interactions between adjacent polymer chains. The hydrogen bonding between such polysaccharides is weakened upon chemical modification to, for example, cellulose ethers (or esters) as a result of the reduced number of hydroxy groups and physical separation between chains caused by the bulk of the additional functional groups (e.g., alkyl groups or ester groups). Structurally modified cellulose can provide material having improved solubility and processability properties. Modified cellulose, such as hydroxyethyl cellulose, hydroxypropyl cellulose, methylcellulose, and like modified cellulose(s), or derivatives thereof, has been used as an associative thickener, emulsifier, and rheology modifier in a variety of industries including food, pharmaceutical, personal care, and paint (ref 2). In addition, Methocel® available from Dow Chemical, films, or other hydroxymethyl-, hydroxyethyl- and hydroxypropyl-cellulose polymers, are known to be cell adhesion resistant (CAR) materials and are used for anchorage independent assays (ref 3). These highly processed materials preferably should have only limited compositional variability, if any.

The in vitro functions (protein production, detoxification) of hepatocytes are dependent on a number of factors including cell-cell contact, substrate bulk modulus, and substrate hydrophobic/hydrophilic balance. Although not bound by theory these parameters should be as tissue-like (soft and hydrophilic) as possible to produce cells whose function more closely resembles their in vivo counterparts. Hepatocytes (liver cells) are anchorage dependent cells so that the cell-substrate interaction can be very significant in determining cell viability.

In primary cells having, for example, little or no proliferation properties, such as hepatocytes, the compositions, articles, and methods of the disclosure are particularly well suited for cell maintenance and functional study. In contrast, cells that are highly proliferative, for example, malignant cancerous cells may less well suited for such maintenance and study where, for example, the cells high proliferative property is inversely proportional to cell function.

The state-of-the-art for liver cell culture and assay is Matrigel™ available from BD Biosciences, and collagen, both of which are animal sourced. Hepatocytes cultured on Matrigel (specifically formulated for hepatocytes) form spheroid aggregates and show enhanced function. Liver cells cultured on collagen are flat and spread, which is advantageous for proliferation but less ideal for function. If the liver cells are sandwiched between two layers of collagen (i.e., a collagen sandwich), the cells adopt a polygonal appearance and show enhanced function. This method requires the careful manipulation of the gel sandwich and the cells are less accessible. However, both Matrigel and collagen are animal sourced and therefore subject to moderate to high lot-to-lot variability. Harvesting cells from Matrigel typically requires the use of a time consuming protocol using enzymes such as trypsin or dispase. The cell harvesting usually results in high cell loss and low yields due to the numerous washes and centrifugation steps required to completely digest the Matrigel.

In embodiments, the present disclosure provides a non-animal sourced, tunable cell culture coatings and its corresponding coated substrates that provides an in vivo-like cell culture and allows for more predictive cell-based assays and easy cell harvesting.

In embodiments the disclosure provides for the use of hydrophobically (hydrophobe) modified water soluble polymers, specifically, hydrophobically modified polysaccharides, including hydrophobically modified hydroxyethyl cellulose or HMHEC such as certain commercially available Natrosol® and PolySurf® products available from Hercules Incorporated, as substrate coatings for the culture and the release of anchorage-dependent cells, such as hepatocytes, including in vitro and encapsulation of non-anchorage dependent cells. These materials are particularly suitable for hepatocyte or other mammalian cells (e.g., primary, cancer) that require lower modulus surfaces that provide greater cell-cell attachment and communication that approach in-vivo-like function.

In embodiments the disclosure provides a cell culture substrate having a surface having attachment points that may be particularly conducive for anchorage dependent cells. The disclosed coatings can be readily prepared and are relatively inexpensive. The disclosed coatings provide substrate coatings that are non-animal derived and the resulting coated products have, for example, less or no lot-to-lot variability. The disclosed coatings provide substrate coatings that can easily incorporate attachment points to covalently link, for example, macromolecules to enhance attachment, enhance function, or reduce oxidative damage arising from, for example, CYP450 activity.

The non-covalent interaction (e.g., hydrogen bonding and hydrophobic interactions) that allows for the cohesiveness of the polymer (e.g., FIG. 1B) in solution weakens over time and thus provide a mechanism for programmable control of the release of cultured cells from the coated surface as disclosed herein.

In embodiments the culture and release properties of the coated articles can be readily "tuned" or beneficially modified by, for example, the selection of the HMHEC compound, such as of chemical structure formula R—HEC (ref. 8):

R-HEC the extent of hydrophobic modification, cross-linking the hydrophobic substituents, incorporation of additives such as amylose, UV/thermally curable structural modifications, and like methods, or combinations thereof. It is also possible to tune the coated substrate's physical properties such as the modulus, HLB, (hydrophilic/lipophilic balance), or both. The disclosed coatings can provide substrate surface coatings having a modulus that can be easily tuned by, for example, cross-linking such as by UV or thermally curable modifications or esterification. The disclosed coating compositions can provide substrate surface coatings that can be non-toxic and biocompatible. The disclosed coating compositions can provide substrate surface coatings that are highly processible, such as easy to deposit onto a variety of surfaces, and provide enhanced adhesion of the coating and of cells to various substrates, for example, a plastic such as poly(methyl methacrylate), polystyrene, acrylonitrile butadiene styrene, polycarbonate, poly(vinyl chloride), polyethylene terephthalates, polyethylene terephthalate esters, polyolefin, cyclic polyolefins, polyvinylidene fluoride, polytetrafluoroethylene, and like materials, glass such as silica, borosilicate, soda lime glass, and like materials, and like cell culture substrates or supports.

In embodiments the disclosure provides a coating composition for cell culture including, for example, a hydrophobe modified polysaccharide comprising a polysaccharide having a plurality of hydrophobes, the hydrophobe having from 6 to about 22 carbon atoms, and the hydrophobes comprise from about 1 to about 20 mole % and the polysaccharide comprises from about 80 to about 99 mole %.

The hydrophobe can be, for example, a $C_{12-20}$ alkyl and the polysaccharide can be, for example, a cellulose. The hydrophobe can also be, for example, a $C_{16-20}$ alkyl and the polysaccharide can be, for example, an hydroxyalkyl cellulose having from 0 to about 3 hydroxyalkyl groups for each saccharide of the polysaccharide, and the hydroxyalkyl group can have, for example, from 2 to about 6 carbon atoms.

In embodiments, the hydrophobe can be, for example, a hydrophobic substituent such as:

—R;

—C(=O)R;

—CH$_2$—CH(OH)—CH$_2$—O—R;

—CH$_2$—CH(OH)CH$_2$—O—C(=O)R; or

—CH$_2$—CH(OH)CH$_2$—C(=O)R, or thiols such as

—S—R,

S—C(=O)R, or S—C(=S)R, and like groups, or combinations thereof, where R is -alkylaryl, -arylalkyl, or a $C_{16-20}$ alkyl having a linear alkyl chain, a branched alkyl chain, a perfluoroalkyl chain, or a mixture thereof. The alkyl chain can be further substituted with a substituent such as an alcohol, an amide, or an ester, or the functional group can be incorporated in the main chain where, for example, a ($C_{4-12}$)alkyl group can be spaced between a group such as an ester, an ether amide, an urethane, an amine, or mixtures thereof.

The polysaccharide can be, for example, a hydroxyethyl modified cellulose having, for example, from 1 to 3 hydroxyethyl groups for each glucose, the hydrophobe can be, for example, a —C(=O)R, where, for example, R is $C_{16-20}$ alkyl, and having, for example, a hydroxyethyl to hydrophobe mole ratio of from about 6:1 to about 1:1. The polysaccharide can be, for example, a hydroxyethyl modified cellulose having from 1 to 3 hydroxyethyl groups for each glucose, the hydrophobe can be, for example, a —C(=O)R, where R is $C_{18}$ alkyl, and having, for example, from about 2 to about 15 mole % hydrophobe and from about 85 to about 98 mole % polysaccharide.

In embodiments the disclosure provides a compound comprising:
a polysaccharide comprised of a hydroxyethyl modified cellulose having from 1 to 3 hydroxyethyl groups for each glucose, and
a plurality of hydrophobes comprised of a —C(=O)R, where R comprises $C_{18}$ alkyl, and having from about 2 to about 15 mole % hydrophobe and from about 85 to about 98 mole % polysaccharide.

In embodiments the disclosure provides a method for cell culture comprising:
providing a substrate coated with the abovementioned hydrophobe modified polysaccharide composition or like compositions;
contacting the coated substrate with a cell culture for a sufficient time to establish functional cells; and
harvesting the cells from the substrate.

In embodiments, the substrate can be, for example, a material selected from a metal oxide, a mixed metal oxide, a synthetic polymer, a natural polymer, or like materials, and combinations thereof In embodiments, the contacting of the coated substrate with a cell culture for a sufficient time to establish functional cells can be, for example, from about 3 to about 14 days for hepatocyte HepG2/C3A cells. The cells can be, for example, released from the coated substrate concurrently with the release of the hydrophobe modified polysaccharide coat from the substrate surface. Accordingly, the disclosure provides a method of using a hydrophobically modified polysaccharide for cell culture and programmed-release or self-release of cultured cells, and without use of enzyme digestion or enzyme assisted release.

The cells of the cell culture can be, for example, any suitable primary cells, or associated immortalized cell lines, of any cell type such as hepatocytes. The cell culture can include, for example, cells actively producing albumin, antibodies, or like entities, and combinations thereof. The harvesting of cells from the substrate can include, for example, simultaneously or concurrently releasing the coating and the surface cultured cells from the substrate.

The release of the coating and the surface cultured cells from the substrate can include, for example, at least one of:
providing a shear thinning force;
providing a clathrate, also known as, for example, a host-guest complex former, an inclusion compound former, and adduct former, and like coating stability disrupters or destabilizers, such as a cyclodextrin, a crown ether, a cryptand, and like entities, or combinations thereof, but not including amylose (a stabilizer). The release of the coating and the surface cultured cells from the substrate can include, for example, pre-selecting the substrate and the aforementioned coated composition to have or provide a surface adhesion half-life of, for example, from about 2 days to about 40 days, from about 3 days to about 20 days, or from about 4 days to about 10 days. Preferably, the coating can have a long life or high stability until just before cell harvesting. The pre-selection of the substrate and the coated composition surface having an adhesion half-life can be, for example, providing a coated composition having at least one of:
a hydrophobe modified polysaccharide having a hydrophobe mol % of from about 10 to about 20 or more, intra-molecular or inter-molecular hydrophobe cross-link interaction or like associative interactions of, for example, from about greater than about 50% based on the total hydrophobes available for cross-link interaction or like associative interactions, or combinations thereof, to increase the adhesion half-life;

a hydrophobe modified polysaccharide having a hydrophobe mol % wt % of from about 1 to about 10, intra-molecular or inter-molecular hydrophobe cross-link interaction or like associative interactions of from about less than about 50% based on the total hydrophobes available for cross-link interaction or like associative interactions, or combinations thereof, to decrease the adhesion half-life;
at least one coating stabilizer;
at least one coating destabilizer;
or combinations thereof The coating destabilizer can be, for example, a clathrate, a hydrophobe sequesterant, an amphiphile such as a zwitterionic compound, a surfactant compound, or a combination thereof. The coating stabilizer can be, for example, a hydrophilic polysaccharide such as a glucose polymer such as amylose, amylopectin, or like polymers.

In embodiments, coating compositions of the disclosure can include, for example, a beta-cyclodextrin, and like compounds, or mixtures thereof, to destabilize or interfere with or weaken actual or potential hydrophobic interactions in the hydrophobe modified polysaccharide coat, such as an HMMEC, and to promote the dissolution or release of the substrate coating and the cells from the substrate. In embodiments, a beta-cyclodextrin, and like compounds or mixtures thereof, can be added to the post-culture media to facilitate release of the substrate coating and associated cells.

The harvesting of cells from the substrate can include, for example,
removing liquid media from the culture;
adding an aqueous liquid to the culture; and
providing a shear force.

In embodiments the disclosure provides a method of making an auto-release cell culture, comprising: providing a substrate; and depositing a hydrophobically modified polysaccharide on the substrate. The depositing can be accomplished with, for example, any suitable coating method. In embodiments the substrate can be, for example, plastic, the hydrophobe modified polysaccharide can be a partially cetyl substituted or alkylated hydroxyethylcellulose or like hydrophobe and cellulose modifications, or combinations, and the depositing can be accomplished with, for example, electrospinning, solution coating, and like coating or film forming methods, or combinations thereof.

In embodiments the disclosure provides a composition for cell culture comprising:
a hydrophobe modified polysaccharide comprising a polysaccharide having a plurality of hydrophobes, the hydrophobe-modified polysaccharide coating having an initial water contact angle greater than or equal to 60°.

HEC Functional Group Modification. Additionally or alternatively, polysaccharides of the disclosure can be further functionally modified with, for example, urethanes, maleimides, esters, functionalized with biological macromolecules, or like groups for increasing or decreasing specific intra- or interchain interactions of hydrophobically modified groups.

The hydroxyl groups of cellulose can be partially or fully reacted with various reagents to afford derivatives with useful cell culture coating properties. Cellulose esters and cellulose ethers are examples of readily available commercial materials. Lower molecular weight modified cellulose esters are known, such as cellulose acetate and cellulose triacetate, which are known film- and fiber-forming materials having various industrial uses. Ether modified cellulose derivatives can be selected as the hydrophobe modified polysaccharide or used as starting material for further hydrophobic derivatization and can include, for example, alkycellulose, such as incompletely alkylated methyl or ethyl cellulose. Other suitable cellulose starting materials can include, for example, hydroxypropyl cellulose, carboxymethyl cellulose, hydroxypropyl methyl cellulose, hydroxyethyl methyl cellulose, and like materials, or combinations thereof.

HMHEC alkyl ethers, hydroxy alkyl ethers, esters, and like hydrophobically linked HECs are commercially available or can be readily prepared using various reactants, see for example, the working examples and above mentioned R—HEC chemical structure and ref. 8. If desired one can append biologic molecules of interest such as peptides, growth factors (such as HGF), antioxidants, glycans, or like molecules to the hydrophobe modified polysaccharides to further modify substrate coating surface properties, such as substrate adhesion, cellular attachment, cell function, cell proliferation, coating release, and cell release properties. The polysaccharide polymer can be further modified using, for example, standard carbohydrate and polymer functionalization techniques to attach a variety of (macro)molecules. For example, one can incorporate a maleimide functional group using a Mitsunobu reaction ($PPh_3$, diethyl azodicarboxylate as catalyst) to easily and selectively attach a thiol-containing molecule, such as cysteine modified polypeptide, to the polymer. Alternatively, any thiol containing compound can be used to add another functional group of interest if a spacer is desired or necessary for proper ligand display.

The abundance of hydroxy groups in the HMHEC allows for polymer modification using ester formation using, for example, coupling reagent combination such as EDC/NHS (N-(3-Dimethylaminopropyl)-N'-ethylcarbodiimide and N-hydroxysulfosuccinimide), or like carbodiimide coupling reagents. A preactived carboxylic acid such as a succinimide ester orp-nitrophenol carbonate ester can also be used in the absence of the coupling reagents.

Any of the aforementioned or like chemistries (ref. 4) can also be used to further modify the polymer with hydrophobe groups. This modification can increase the hydrophobic interaction(s) between the polysaccharide chains and permit tuning of useful cell culture time and coating release from the substrate. Other self-associating groups, such as perfluoroalkyl or silicone, can be incorporated into the coating formulation to provide additional coating cohesion, but not cell adhesion, particularly if there is an interest in probing specific ligand-receptor interactions.

Additionally or alternatively, polysaccharides of the disclosure and like materials can be functionally modified using, for example, maleimide chemistry, esterification, functionalization of biological macromolecules, or like methods for increasing specific intra- or interchain interactions of hydrophobically modified groups. If desired one can append biologically relevant molecules such as peptides, growth factors (such as HGF), antioxidants, glycans or like entities to the cellulose polymers to modify, for example, cellular attachment, function, and proliferation.

Alternative Polymers Other water soluble polymers including, for example, poly(vinyl alcohol), poly(acrylamide), poly(acrylic acid), and linear or branched polysaccharides including, for example, dextran, agarose, chitosan, amylose, amylopectin and like polymers can be selected as additives or can be chemically modified with hydrophobic or like associating groups, including self-complexing and complementary binding pairs, to produce tunable, for example, viscoelastic coatings having hydrogel-like properties that are suitable for cell culture and assay. Further fine tuning of the substrate coating properties with respect to, for example, the cell type, assay, and release, can be accomplished by, for example, combining one or more of the examples mentioned above or disclosed herein.

The disclosure provides, in embodiments, hydrophobe modified polyssacharides, including certain modified celluloses, as a material for cell culture that provides in vivo-like conditions that can enhance cellular function. The substrate coatings can include hydrophobe modified polysaccharides, and other polymers such as poly(vinyl alcohol) and poly(acrylamide), that are water soluble and modified with hydrophobe groups to provide cohesive non-covalent crosslinking interactions.

In embodiments, the disclosure provides a hydrophobe derivatized polysaccharide for cell culture substrate coating for anchorage-dependent cells and the subsequent release of the cultured cells from these materials, such as Natrosol® and other HMHEC coated substrates. The hydrophobe derived polysaccharide can be used as-is, for example, to produce thin film surfaces to culture cells, as a gel to encapsulate cells or cell clusters, or like applications. The film can be strengthened by reinforcing the existing hydrophobic interactions present between the polymer chains or the film strength can be weakened by destroying interchain binding by using competitive interactions, such as by including a destabilizing additive. With chemical functionalization, biologically relevant macromolecules or ligands can be attached. In embodiments the polymer can be crosslinked and made into 3-dimensional scaffolds.

Figure 1A:
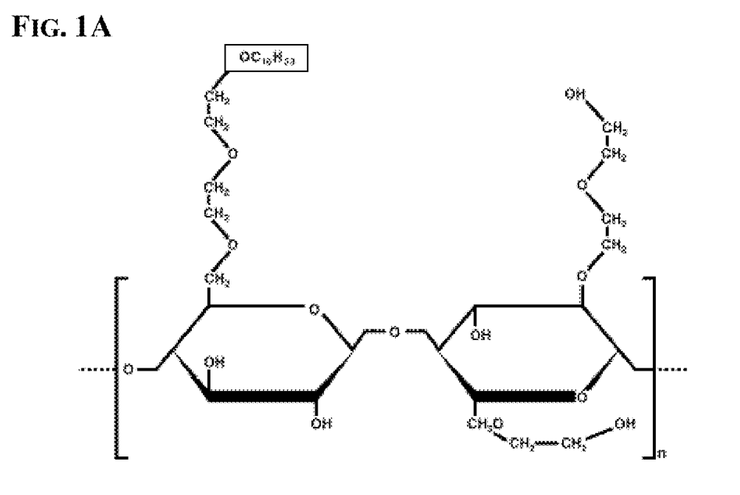
FIGS. 1A and 1B include a representation of a hydrophobically modified hydroxyethylcellulose (HMHEC), and a representation of gel formation in solution via hydrophobic interactions between the alkyl side chains of the HMHEC, respectively, in embodiments of the disclosure.
Figure 1B:
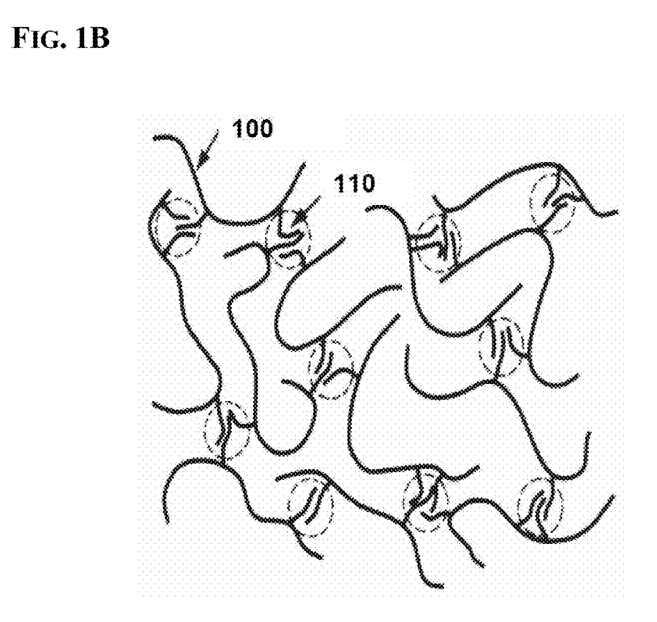

In embodiments, various biocompatible polymer materials can additionally be used in combination or in admixture with the HMMEC compounds and compositions of the disclosure, and can include, for example, polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, and copolymers thereof, nitro celluloses, polymers of acrylic and methacrylic esters, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacrylate), poly(ethylmethacrylate), poly(butylmethacrylate), poly(isobutylmethacrylate), poly(hexylmethacrylate), poly(isodecylmethacrylate), poly(laurylmethacrylate), poly(phenylmethacrylate), poly(methacrylate), poly(isopropacrylate), poly(isobutacrylate), poly(octadecacrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyhyaluronic acids, casein, gelatin, gluten, polyanhydrides, polyacrylic acid, alginate, chitosan, and any copolymers thereof, and any combination thereof Referring to the Figures, FIG. 1 includes a representation of a hydrophobically modified hydroxyethylcellulose (HMHEC) chemical structure (FIG. 1A), and a representation of gel formation in solution via hydrophobic interactions between the alkyl side chains of the HMHEC (FIG. 1B), respectively.

Figure 2A:
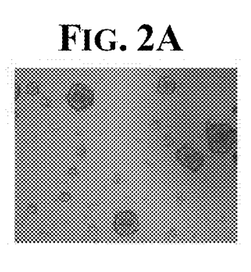
FIGS. 2A-2C shows photo images of HepG2/C3A cells after 7 days of culture on examples of HMHEC thin film coatings, in embodiments of the disclosure.
Figure 2B:
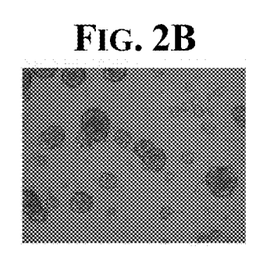
Figure 2C:
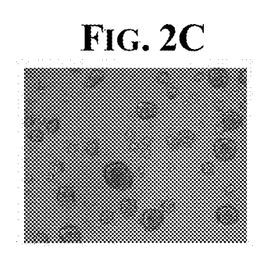

FIG. 2 shows photos of HepG2/C3A cells after 7 days of culture on examples of HMHEC thin film coatings. The cells form clusters that are attached to the Natrosol® coated substrates: FIG. 2A is a N330 coated substrate, FIG. 2B is a N340 coated substrate, and FIG. 2C is a N430 coated substrate.

Figure 3:
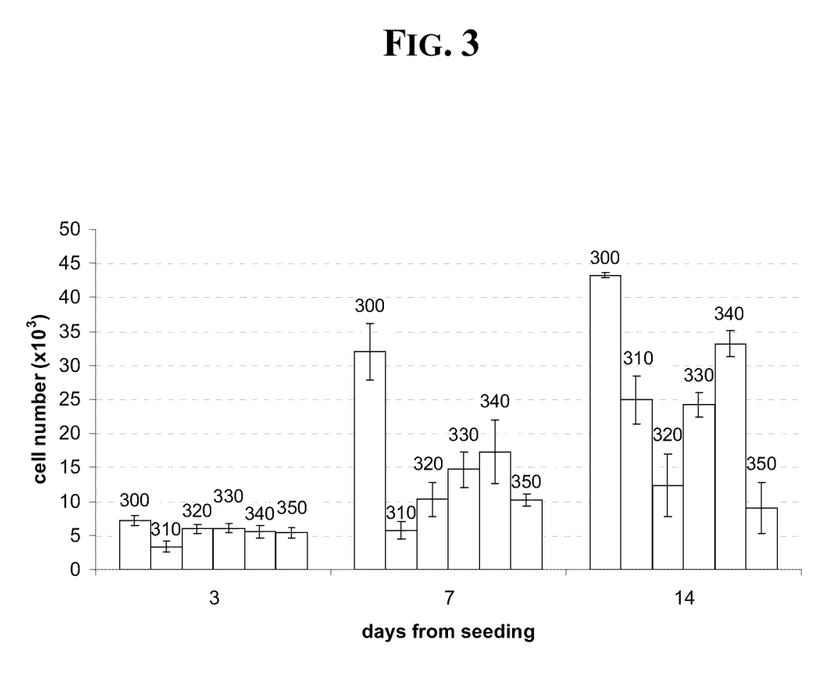
FIG. 3 shows examples of a Promega MTS assay on HepG2/C3A cells cultured on exemplary HMHEC films after 3, 7, and 14 days of culture, in embodiments of the disclosure.

FIG. 3 shows examples of a Promega MTS assay on HepG2/C3A cells cultured on various HMHEC thin films after 3, 7, and 14 days, respectively, of culture. Cells cultured contemporaneously on tissue culture treated (TCT) polystyrene, for example, in a 96-well plate format available from Corning Inc, were used as a control. The results showed that HepG2/C3A cells attach to the HMHEC coatings (310, 320, 330, 340, and 350) of the disclosure and proliferate at a moderate rate (slower than cells on TCT) which can be advantageous, for example, in cell function studies, such as albumin production described below. Hence, an initial contact angle (Table 2) of ≥60° may be significant for cell attachment and limiting proliferation for HMHEC-type polymer coatings. The samples and corresponding reference numerals are: TCT (300), N100 (310), N330 (320), N340 (330), N430 (340), and PS67 (350), where N is a Natrosol® and PS is PolySurf®.

Figure 4A:
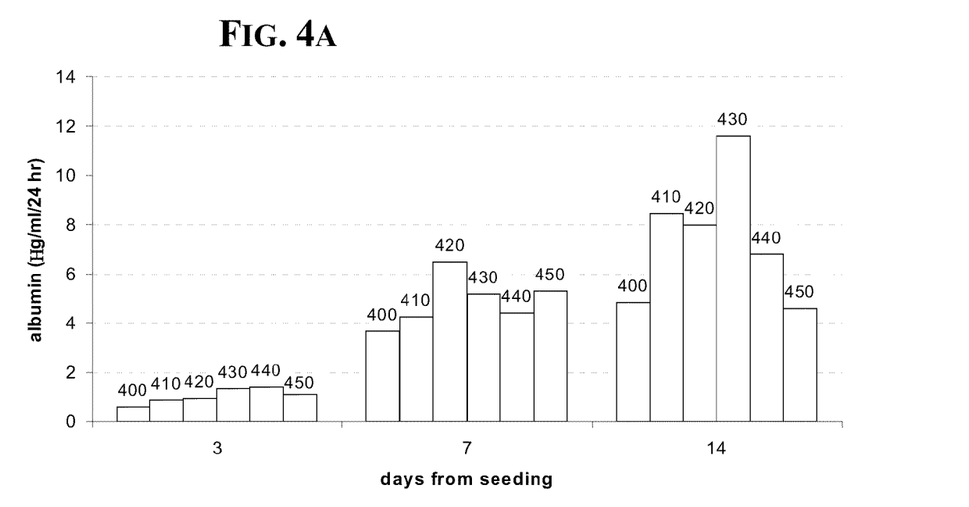
FIGS. 4A-4B shows albumin production of HepG2/C3A cells on HMHEC coated substrates compared with cells cultured on a tissue culture treated (TCT) polystyrene substrate by total albumin production per day per mL (FIG. 4A) or normalized to cell number (FIG. 4B), in embodiments of the disclosure.
Figure 4B:
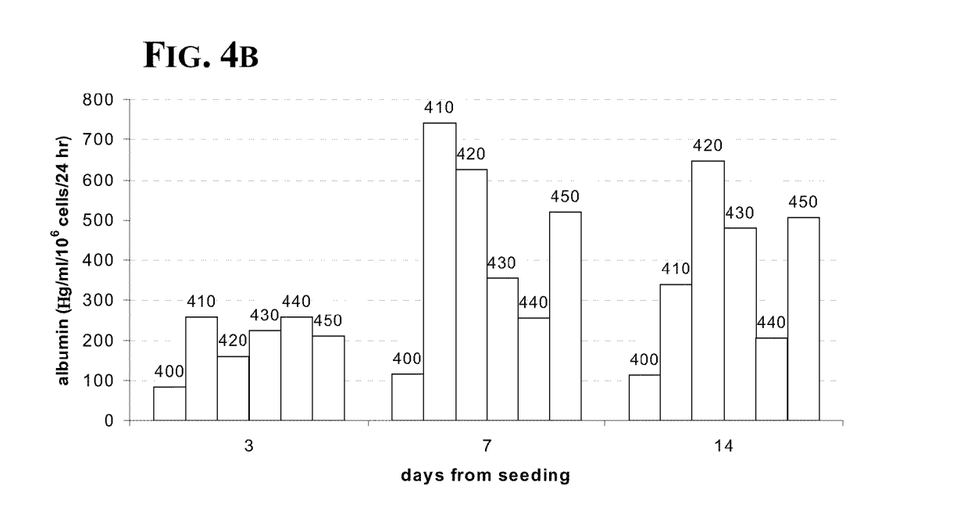

FIGS. 4a and 4b show albumin production of HepG2/C3A cells on exemplary HMHEC coated substrates compared with cells cultured on TCT (control) by total albumin production per day per mL (FIG. 4a) or normalized to cell number (FIG. 4b). In all cases, the albumin production for cells cultured on HMHEC coated substrates of the disclosure is from about 2 to about 6 times better per million cells than cells cultured on TCT. The samples and corresponding reference numerals are: TCT (400), N100 (410), N330 (420), N340 (430), N430 (440), and PS67 (450).

Figure 5:
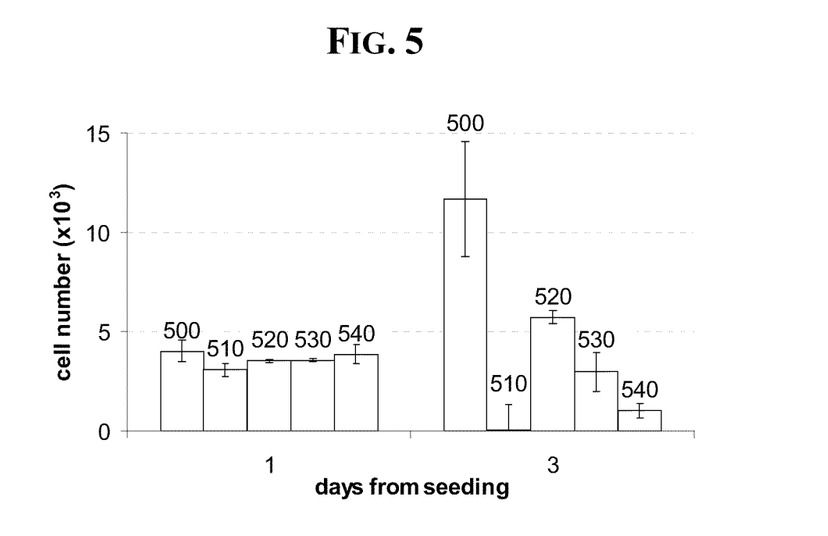
FIG. 5 shows time dependent cell attachment on a series of four HMHEC coated substrates, in embodiments of the disclosure.

FIG. 5 shows cell attachment on a series of HMHEC coated substrates of the disclosure. The samples and corresponding reference numerals were: a tissue culture treated control (TCT)(500), 5% lauryl (510), 8% lauryl (520), 10% lauryl (530), and 15% lauryl (540), where % is the % hydrophobicity and is defined as the number of added lauryl hydrophobe groups relative to the glucose/monomer unit, and not by number of possible hydroxy reaction sites. Thus, for example, a 5% lauryl modification is equivalent to about 1 lauryl group for every 20 glucose monomer units, a 10% lauryl is equivalent to about 2 lauryl groups for every 20 glucose monomer units, a 20% lauryl is equivalent to about 4 lauryl groups for every 20 glucose monomer units, and like percent modifications. The experimental results are described below in Example 3. The initial attachment of cells on the synthesized HMHEC polymer coatings on TCT is similar to that on TCT whereas the proliferation rate is lower based on cell number. The results show that greater than about 5% lauryl modification of the HEC provides superior results for cell retention.

Figure 6:
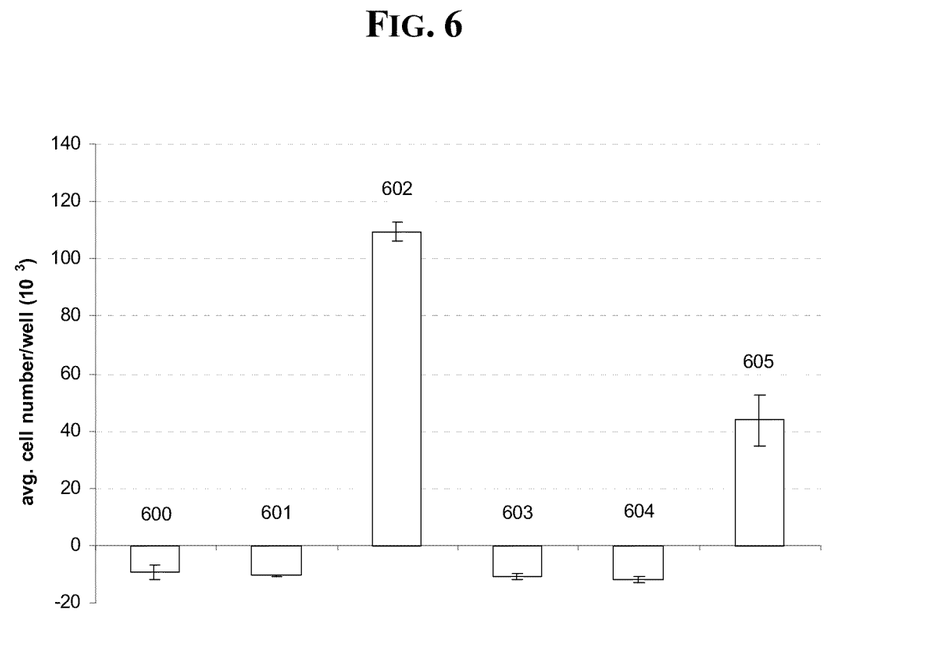
FIG. 6 shows cell attachment as the number of cells remaining after media change (controls) and the lack of cells remaining (release) in coated wells after cell harvest, in embodiments of the disclosure.

FIG. 6 shows cell attachment results of coated substrates: on PS67 after media change (602, no shear applied to cells), on PS67 (run in duplicate) after harvesting via applied shear through pipetting (600, 601), on N330 after media change (605, no shear applied to cells), and on N330 (run in duplicate) after harvesting via applied shear through pipetting (603, 604). Photo microscopic images of the surface after cell release using pipette shear thinning showed no cells present, and the controls (602, 605) showed cells present (photos not shown). The results show the advantage of culturing cells on HMHEC surfaces where the cells can be harvested through applying shear force and not require the use of enzymatic digestion.

EXAMPLES

The following examples serve to more fully describe the manner of using the disclosure, and to further illustrate and demonstrate specific examples of best modes contemplated for carrying out various aspects of the disclosure. These examples do not limit the scope of the disclosure, but rather are presented for illustrative purposes.

Example 1

Hydrophobic Modification of Hydroxyethylcellulose (HMHEC) with an Alkyl Acid Chloride Materials: hydroxyethylcellulose ("HEC", CELLOSIZE QP 30; available from Dow Chemical, acid chloride functionalized alkyl group (or other hydrophobic groups), N-methylpyrrolidone (NMP), isopropyl alcohol (IPA) and acetone.

Procedure: The hydroxyethylcellulose was pre-dried for about 16 hours at room temperature under $CaSO_4$ or vacuum. The hydroxyethylcellulose was dissolved in NMP (e.g., about 100 mg HEC/5 mL NMP). Dissolution can typically be facilitated with gentle warming, stirring, or both. Next, the acid chloride in diluted with NMP to obtain a workable solution or suspension. The acid chloride solution was added dropwise with stirring to the hydroxyethylcellulose and NMP solution and stirred at room temperature for about 2 hours or more. The reaction mixture was poured into acetone and stirred in a closed container to exclude moisture for about 30 min to precipitate a product. The acetone solvent can be replaced or mixed at higher hydrophobic modifications, for example, mixed with or replaced by methanol or like organic solvents. The crude precipitate was filtered and washed with acetone (or like wash solvent) then dried at 60° C. in an oven or a heated or ambient vacuum desiccator. In instances where greater product purity is desired, the product can be dissolved in, for example, NMP or other suitable dissolving non-aqueous solvent or solvent mixtures, to reprecipitate. The isolated product can be stored in sealed container at room temperature.

Example: HEC (300 mg) in NMP (15 mL); Lauryl acid chloride stock solution (0.5 mL in 9.5 mL NMP); About 0.1 mL of lauryl acid chloride stock solution was added to the HEC. The isolated product, lauryl-HEC, was off-white powder, and was obtained in an isolated yield of about 90%. The amount of lauryl groups in the copolymer was determined by $^1H$ NMR integration. At the lower concentrations, the integration is more difficult because of lower signal to noise ratio.

TABLE 1

Lauryl acid chloride hydrophobic modification of hydroxyethylcellulose.

| Lauryl acid chloride (mL) | mol % Lauryl derivatization (hydrophobicity (%)) |
|---|---|
| 0.6 | 2.9 |
| 1 | 3.2 |
| 1.33 | 4.9 |
| 1.67 | 8.1 |
| 2 | 10.1 |
| 2.5 | 15.1 |

TABLE 2

Properties of Commercially available HMHEC compounds.

| HMHEC Compound | Molecular Weight | Viscosity (P) | Contact Angle | Zeta Potential (mV) |
|---|---|---|---|---|
| N100 | NA | 0.12 +/− 0.06 | 43.7 +/− 2.2 | −7.5 +/− 0.6 |
| N330 | 350,000 | 0.80 +/− 0.11 | 96.8 +/− 1.5 | −7.0 +/− 1.1 |
| N340 | NA | 0.64 +/− 0.06 | 95.5 +/− 2.0 | −3.1 +/− 0.6 |
| N430 | NA | 0.93 +/− 0.05 | 97.6 +/− 2.8 | −3.1 +/− 0.2 |
| PS67 | 550,000 | 1.15 +/− 0.17 | 61.1 +/− 2.5 | −6.3 +/− 0.8 |

The viscosity of HMHEC compounds was measured on a Brookfield CAP 2000 Viscometer (rotational), at 250 rpm and 25° C. Samples were prepared by dissolving 100 mg material in 10 mL DI water. The contact angle measurements were obtained on a Rame-Hart goniometer (Rame-Hart Instrument Company, Netcong, N.J.) and measured within one minute to obtain the measurement before hydration, that is the initial contact angle. The zeta potential measurements were obtained on a Brookhaven Instruments Electro Kinetic Analyzer (EKA) (Brookhaven Instruments, Holtsville, N.Y.).

In embodiments having coatings hydrophobically modified HECs with higher percentages of hydrophobic modification, such as % hydrophobicity of from about 30 to about 50%, or more, the coated films can be further destabilized for release, or destabilization can be accelerated, by contacting the coating with an additive such as beta-cyclodextrin, or like clathrate compound or cage compound. These materials can interact with and disturb or destroy the inter- or intra-molecular hydrophobic interactions of the hydrophobically modified HEC coating compound(s) which can in turn disturb the gel properties and disturb the integrity of the substrate coating, and increase coating dissolution and rates of cell release.

Example 2

Hydrophobic Modification of Hydroxyethylcellulose (HMHEC): Methacrylic Anhydride Materials: hydroxyethylcellulose ("HEC"; Dow QP30), methacrylic anhydride, NMP, and acetone.
Procedure: The hydroxyethylcellulose was pre-dried in a desiccator for about 16 hours. The hydroxyethylcellulose was dissolved in NMP (e.g., about 100 mg HEC/5 mL NMP). Dissolution can typically be facilitated with gentle warming, stirring, or both. Next, the methacrylic anhydride was diluted with NMP to obtain a workable solution or suspension at about 10 fold dilution. The methacrylic anhydride solution was added dropwise with stirring to the hydroxyethylcellulose and NMP solution and then stirred at room temperature for about 2 hours or more. The reaction mixture was poured into acetone and stirred in a closed container to exclude moisture for about 30 min to precipitate a product. In examples having higher hydrophobic modification the acetone solvent can be replaced-by or mixed-with methanol. The crude precipitate was filtered and washed with acetone (or like wash solvent) then dried at 60° C. in an oven or a heated or ambient vacuum desiccator. In instances where greater product purity is desired, the product can be dissolved in, for example, NMP or other suitable dissolving non-aqueous solvent or solvent mixtures, to reprecipitate. The isolated product can be stored at room temperature in sealed container that excludes light.

The resulting methacrylate modified HEC can be used to coat substrates, and optionally further reacted or derivatized with, for example, a hydrophobe, a charged group, or in a crosslinking reaction to further modify the coated substrate's cell culture and release properties (see e.g. Example 6).

Example 3

HMHEC Thin Film Coatings A hydrophobe modified cellulose polymer in an amount of, for example, 0.2 wt % HMHEC (such as either PolySur® 67 or Natrosol® 430, or like synthetically prepared or commercially available polymers), was dissolved in deionized water and coated on an appropriate cell culture vessel consisting of, for example, a polystyrene, a cyclic olefin, a poly(ethylene), and like materials, or combinations thereof, or their tissue culture treated versions such as available from Corning® Inc., including, for example, flasks, petri dishes, well plates, slides, and like surfaces, using standard coating methods such as drop casting, dip coating, spin coating, and like methods to apply a thin film. Substrate coating or film thickness and thickness ranges are not easily measured because the coatings swells on contact with water, but are estimated to be, for example, from about 0.2 to about 1.0 mm, or about 0.3 to about 0.5 mm. Upon drying, the coatings are stable under ambient conditions and can be sterilized using typical sterilization techniques such as an ethanol wash, and UV or gamma irradiation.

The thin films prepared from PolySurf® or Natrosol® have a built-in period of useful cell culture time. Stability in liquid culture media is typically 7 days depending on amount of hydrophobic groups and molecular weight of the polymer. After this time, the film swells and becomes more soluble and cells can be easily harvested from the cell culture vessel. The working time of the coated substrate can be further tuned (see Example 6).

Cells (HepG2/C3A) cultured on a HMHEC coated substrate form multicellular aggregates, that is spheroid-like, see FIG. 2, with similar morphology to those cultured on other soft, hydrophilic coatings such as Matrigel. Cell proliferation on these HMHEC coated substrates is low compared to cells cultured on TCT (see FIG. 3). The lower proliferation rate can be advantageous in cell function studies. Albumin produced per mL (or well), however, was higher than for the TCT substrate, indicating for example higher function which can be significant inAdMETox assays, even though fewer cells were present (see FIG. 4) that is, cell proliferation is low or non-existent while albumin production remains active and cell function is viable. Liquid culture medium was typically replaced daily or every 2 days for albumin.

The initial attachment of cells on the HMHEC polymer coatings on TCT was similar to that on TCT (see FIG. 5) whereas the proliferation rate is lower based on cell number. Cell retention appears to be optimal around 8% hydrophobe modification (see Table 1). Hence, an initial contact angle of greater than or equal to about 60° appears to be optimal for cell attachment and limits proliferation for HMHEC-type polymer coatings.

Typical substrate casting procedure A HMHEC polymer (400 mg) was completely dissolved in deionized water (200 mL) by stirring vigorously for a few hours. The polymer solution (100 microliters per well) was added to a 96-well plate. The solution was allowed to evaporate either under ambient conditions or at elevated temperatures (e.g., 60° C.) until dry. The plates were sterilized by UV irradiation (1 hr at 366 nm) using a UVGL-58 portable UV lamp (UVP, Upland, Calif.) with the plate at about 10 cm from the lamp. Examples of contact angles of, for example, commercially available hydrophobe modified HEC materials when casted as film coatings are illustrated in Table 2 above. The HMHEC coatings of the disclosure are initially hydrophobic (i.e. having a high contact angle). However, upon hydration and continued exposure to water the surface becomes more hydrophilic as measured by decreasing contact angle, and the coatings become progressively more labile as illustrated herein.

Typical cell culture conditions HepG2/C3A cells (American Type Culture Collection (ATCC) # CRL-10741, Manassas, Va.) were cultured in Eagle's Minimum Essential Medium (ATCC #30-2003) supplemented with 10% Fetal Bovine Serum (Invitrogen #16000-077, Grand Island, N.Y.) and 1% penicillin-streptomycin (Invitrogen #15140-155). Cells were incubated at 37° C., in 5% $CO_2$ and 95% relative humidity.

Cells were seeded on the hydrophobe modified cellulose coatings at 5,000 cells in 100 microL media per well in a 96-well microplate format. Liquid media was replaced daily. Liquid media aliquots were taken at assigned intervals and assayed for albumin production. Albumin levels were determined using Micro-Albumin Quantitative Test (Biomeda #

EU-1057, Foster City, Calif.). CellTiter96® Aqueous One Solution MTS assay (Promega # G3581, Madison, Wis.) was used for quantifying cell number.

MTS procedure MTS is short for 3-(4,5-dimethylthiazol-2-yl)-5(3-carboxymethonyphenol)-2-(4-sulfophenyl)-2H-tetrazolium. In the MTS assay procedure a CellTiter96® Aqueous One Solution Cell Proliferation Assay was used to calculate cell number. The MTS reagent was thawed for 10 mins in a 37° C. water bath, and protected from light. For 96-well plates containing 100 μL cell culture media, 20 μl of reagent (or 20% by volume) was added directly to each well. Plates were then mixed thoroughly using a plate shaker and were held at 37° C. for 1 hour. The plates were read on a standard microplate reader at 490 nm. Blank absorbencies were subtracted from test absorbencies and then graphed. A previously prepared standard curve was used to calculate relative cell number for test substrates.

Example 4

Gel and Gel Sandwich Natrosol® and like HMHECs of the disclosure can additionally or alternatively be used to encapsulate cells or cell clusters. The HMHEC powder, for example, can be directly dissolved in culture media, autoclaved, and then poured into, or used to coat, the cell culture vessels. Depending on the strength of the gel and, for example, on the amount and type of HMHEC, cells will either reside at the surface (having higher modulus) or sink (having a lower modulus) into the gel. Alternatively, an additional layer can be poured onto a layer of cells if a sandwich configuration is desired.

Example 5

3D Porous Material A 3D porous scaffold having, for example, a crosslinked HMHEC of the disclosure, or like material, can be selected as a coated substrate. This scaffold can be made using a variety of different methods including, for example, freeze-thawing and freeze-drying, which are typically used methods to obtain porous material for polysaccharides, such as alginates. Alternatively, a solution containing a HMHEC can be electrospun to create a web-like scaffold.

Example 6

Adjustable Working Time or Useful Cell Culture Half-Life of HMHEC Coatings

The HMHEC film or gel integrity can be improved, and modulus of the film, for example when measured at higher hydrophobicities, can be finely-tuned by, for example, the addition of crosslinkers such as covalent, non-covalent, or both. Succinic anhydride, succinic acid, or other like multifunctional carboxylic acids, can be used in conjunction with water soluble carbodiimides such as EDC to chemically crosslink the polysaccharides. The polysaccharide can also be modified using, for example, a UV active monomer such as glycidyl methacrylate so that the resulting monomer modified polymer can be dissolved in solution or hydrated in a colloidal suspension, and then crosslinked, such as with UV irradiation, after the material has been coated.

HMHEC cohesion can also be improved by reinforcing the hydrophobic interactions, for example, as shown in FIG. 1B. For example, amylose (i.e., non-covalent helical clathrate) can form inclusion complexes by wrapping around the alkyl chains of the HMHEC to strengthen the hydrophobic interactions by further stabilizing them.

β-CD ADDITIVE In embodiments the disclosure contemplates use of cyclodextrin or like derivatives, and like oligomeric and polymeric forms, and their derivatives. Hydroxypropyl β-cyclodextrin (β-CD) was tested, with modulus measurements, as a gentle cell release agent for hydrophobe modified water soluble polymers, specifically, hydrophobe modified polysaccharides, including hydrophobe modified hydroxyethyl cellulose or HMHEC, such as Natrosol® and PolySurf®, and like hydrophobe modified polymeric and coating materials. The added cyclodextrin encapsulates hydrophobic moieties at the surface of the coating and allows for the attachment of proteins and renders the surface neutral, hydrophilic, more water soluble, and cell non-attaching.

Amylose Additive Amylose, a polymer of glucose (like cellulose) where the glucose units are attached through $\alpha(1\rightarrow4)$ glycosidic linkage, allows for the formation of alpha helical structures in the presence of appropriate guest molecules. Like cyclodextrins, amylose helices include a hydrophilic exterior and a relatively hydrophobic interior for complexing guests. Without such guest molecules around amylose exists as a random coil in solution. A film can be made by casting the combined amylose solution with HMHEC solutions. Upon hydration, the film appears stable for weeks, by visual inspection, without any apparent dissolution of the material. Thus, amylose can be selected as an additive to increase coated film stability or to balance or off-set coated film destabilizer materials, such as β-CD.

Example 7

Coat and Cell Release from HMHEC Coated Substrates HMHECs are shear sensitive. Accordingly, cells can be harvested from the HMHEC coated surface by, for example, introducing shear force to break apart the nonspecific hydrophobic interactions that stabilize the gel-like surface coating. In the above Example 3, a 24-well microplate was coated with solutions (0.2 wt % in water, 0.5 mL per well) of PolySur® 67 (PS67) in half of the wells of the plate and N330 in the other half of the wells of the plate. The solutions were allowed to completely dry in a 60° C. oven. The plates were sterilized for 1 hr using UV irradiation. Cells were seeded at 100 k (100,000 cells) per well and were allowed to attach to the coated substrate over 24 hrs. Some of the wells were reserved for use as controls. The cell culture media was changed-out to remove any unbound cells. In the sample cell culture wells, the liquid media was pipetted, for example, 10 times to produce shear force to promote or further accelerate the dissolution of the HMHEC polymer surface coating. Since the cells were attached to the now surface liberated hydrophobe modified polysaccharide coating material, the cells were removed upon removal of the media. FIG. 6 shows the MTS data that approximates the cell numbers of both the control (602, 605) and harvested sample wells (600, 601, 603, and 604) where all the cells were removed with repeated gentle pipetting.

The disclosure has been described with reference to various specific embodiments and techniques. However, it should be understood that many variations and modifications are possible while remaining within the spirit and scope of the disclosure.

REFERENCES

1. See generally: http://www.cyprotex.com/products/ADME%20Guide%20.pdf in Cyprotex publication library for general ADMETox information; and Vanhaecke, T., et al., "Hepatocyte Cultures in Drug Metabolism and Toxicological Research and Testing," *Cytochrome P450 Protocols* in Methods in Molecular Biology Series, and Phillips, I., et al., Eds. Methods in Molecular Biology Series 320, Humana Press Inc., Totowa, N.J., 2006, pp. 209-227.
2. LeCluyse, E. L. *European J. Pharm. Sci.*, 2001, 13, 343-368.
3. Moghe, Prabhas V., et al., "Culture matrix configuration and composition in the maintenance of hepatocyte polarity and function," *Biomaterials*, 1996, 17, 373-385.
4. Commonly owned and assigned copending patent application, U.S. Provisional Application Ser. No. 60/906,168, filed Mar. 9, 2007, entitled "Coatings for Cell Culture Surfaces" (SP07-055P).
5. Hercules (www.herc.com/aqualon/aq_markets.html)
6. http://www.lbl.gov/lifesciences/BissellLab/labprotocols/anchorage.htm (Lawrence Berkeley Laboratories, Life Sciences Division)
7. Zhang, L.-M., *Carbohydr. Polym.*, 2001, 45, 1-10.
8. Kawakami, et. al., "Salt Tolerance of an Aqueous Solution of a Novel Amphiphilic Polysaccharide Derivative," *Langmuir*, 2006, Vol. 22, No. 7, 3337; Ihara, et. al., "Solution Properties of a Novel Polysaccharide Derivative," *Chem. Lett.*, 2004, Vol. 33, No. 9, 1094 (mentions a hydrophobically (stearyl alkyl group) modified hydroxyethylcellulose, R—HEC, a glycidal ether and stearyl alcohol adduct); Akiyama, et al., *J. Colloid Interface Sci.*, 2005, 282, 448.

What is claimed is:

1. A destabilizable cell culture coated substrate comprising:
a substrate coated with a gel composition comprised of:
a hydrophobe modified polysaccharide comprising a polysaccharide having a plurality of hydroxyalkyl groups, and having a plurality of hydrophobes bonded to the hydroxyalkyl groups, the hydrophobe having from 6 to about 22 carbon atoms, and the hydrophobes comprise from about 1 to about 20 mole % of the hydrophobe modified polysaccharide and the polysaccharide comprises from about 80 to about 99 mole % of the hydrophobe modified polysaccharide based on 100 mol % of the hydrophobe modified polysaccharide, wherein the gel composition when destabilized releases cells cultured on the coated substrate.

2. The cell culture coated substrate of claim 1 wherein the hydrophobe comprises a $C_{12-20}$ alkyl and the polysaccharide comprises a cellulose.

3. The cell culture coated substrate of claim 1 wherein the hydrophobe is selected from the group consisting of:
—R;
—C(=O)R;
—$CH_2$—CH(OH)—$CH_2$—O—R;
—$CH_2$—CH(OH)$CH_2$—O—C(=O)R; and
—$CH_2$—CH(OH)$CH_2$—C(=O)R,
or a combination thereof where R is a $C_{16-20}$ alkyl having a linear alkyl chain, a branched alkyl chain or a mixture thereof.

4. The cell culture coated substrate of claim 1 wherein the polysaccharide comprises a hydroxyethyl modified cellulose having from 1 to 3 hydroxyethyl groups for each glucose, the hydrophobe comprises a —C(=O)R, where R is $C_{16-20}$ alkyl, and having a hydroxyethyl to hydrophobe mole ratio of from about 6:1 to about 1:1.

5. The cell culture coated substrate of claim 1 wherein the polysaccharide comprises a hydroxyethyl modified cellulose having from 1 to 3 hydroxyethyl groups for each glucose, the hydrophobe comprises a —C(=O)R, where R is $C_{18}$ alkyl, and having from about 2 to about 15 mole % hydrophobe and from about 85 to about 98 mole % polysaccharide based on 100 mole % of the hydrophobe modified polysaccharide.

6. The cell culture coated substrate of claim 1 wherein a portion of the hydrophobe modified polysaccharide is cross-linked.

7. A destabilizable cell culture coated substrate comprising:
a hydrophobe modified polysaccharide dry gel surface coating that coats the substrate comprising a polysaccharide having a plurality of hydrophobes, the hydrophobe-modified polysaccharide dry gel coated substrate having an initial water contact angle greater than or equal to 60° measured prior to rehydration, wherein the hydrophobe modified polysaccharide comprises a polysaccharide having a plurality of hydroxyalkyl groups, and having a plurality of hydrophobes bonded to the hydroxyalkyl groups, the hydrophobe having the formula —C(=O)R and R is alkyl having from 6 to about 22 carbon atoms.

8. The cell culture coated substrate of claim 7 wherein a portion of the hydrophobe modified polysaccharide is cross-linked.

9. A method for cell culture comprising:
providing a substrate coated with a gel comprised of a hydrophobe modified polysaccharide composition comprising:
a hydrophobe modified polysaccharide comprising a polysaccharide having a plurality of hydrophobes, the hydrophobe having the formula —C(=O)R and R is from 6 to about 22 carbon atoms, and the hydrophobe comprises from about 1 to about 20 mole % of the hydrophobe modified polysaccharide and the polysaccharide comprises from about 80 to about 99 mole % of the hydrophobe modified polysaccharide based on 100 mole % of the hydrophobe modified polysaccharide;
contacting the coated substrate with a cell culture for a time to establish functional cells; and
harvesting the cells from the substrate.

10. The method of claim 9 wherein the substrate comprises a material selected from a metal oxide, a mixed metal oxide, a synthetic polymer, a natural polymer, or combinations thereof.

11. The method of claim 9 wherein the cell culture comprises hepatocytes.

12. The method of claim 9 wherein the cell culture comprises cells actively producing albumin, antibodies, or combinations thereof.

13. The method of claim 9 wherein harvesting cells from the substrate comprises releasing the coating and the surface cultured cells from the substrate.

14. The method of claim 13 wherein releasing the coating and the surface cultured cells from the substrate comprises at least one of:
providing a shear thinning force;
providing a destabilizing clathrate; and combinations thereof.

15. The method of claim 13 wherein releasing the coating and the surface cultured cells from the substrate comprises pre-selecting the substrate and coated composition to have a surface coating adhesion half-life of from about 3 days to about 20 days.

16. The method of claim 15 wherein pre-selecting the substrate and coated composition surface adhesion half-life comprises providing a coated composition having at least one of:

a hydrophobe modified polysaccharide having a hydrophobe mol % of from about 10 to about 20, intra-molecular or inter-molecular hydrophobe cross-link interaction of from about greater than about 50% based on the total hydrophobes available for cross-link interaction, or combinations thereof, to increase the adhesion half-life;

a hydrophobe modified polysaccharide having a hydrophobe mol % of from about 1 to about 10, intra-molecular or inter-molecular hydrophobe cross-link interaction of from about less than about 50% based on the total hydrophobes available for cross-link interaction, or combinations thereof, to decrease the adhesion half-life;

at least one coating stabilizer;

at least one coating destabilizer;

or combinations thereof.

17. The method of claim 16 wherein the at least one coating destabilizer comprises a clathrate, a hydrophobe sequesterant, an amphiphile, or a combination thereof, and the coating stabilizer comprises a hydrophilic polysaccharide.

18. The method of claim 9 wherein harvesting cells from the substrate comprises:
   removing liquid media from the culture;
   adding an aqueous liquid to the culture; and
   providing a shear force.

19. The method of claim 9 wherein contacting the coated substrate with a cell culture for a time to establish functional cells comprises from about 3 to about 14 days for HepG2/C3A cells.

20. The method of claim 9 wherein the cells release from the coated substrate concurrently with the release of the hydrophobe modified polysaccharide coat from the substrate.

* * * * *